United States Patent
Wildermann et al.

(10) Patent No.: US 8,003,843 B2
(45) Date of Patent: Aug. 23, 2011

(54) TRANSPORT OF ETHYNE IN FORM OF α-ALKYNOLS AS ETHYNE PRECURSORS

(75) Inventors: Angela Wildermann, Bad Säckingen (DE); Werner Bonrath, Freiburg (DE); Gunther Hellmann, Laufenburg (DE)

(73) Assignee: DSM IP Assets B.V., Heerlen (NL)

( * ) Notice: Subject to any disclaimer, the term of this patent is extended or adjusted under 35 U.S.C. 154(b) by 395 days.

(21) Appl. No.: 12/298,371

(22) PCT Filed: Mar. 30, 2007

(86) PCT No.: PCT/EP2007/002885
§ 371 (c)(1),
(2), (4) Date: Jan. 15, 2009

(87) PCT Pub. No.: WO2007/121826
PCT Pub. Date: Nov. 1, 2007

(65) Prior Publication Data
US 2009/0221860 A1    Sep. 3, 2009

(30) Foreign Application Priority Data
Apr. 25, 2006 (EP) .................................. 06008477

(51) Int. Cl.
*C07C 7/20* (2006.01)

(52) U.S. Cl. ..................................................... 585/899
(58) Field of Classification Search .................. None
See application file for complete search history.

(56) References Cited

U.S. PATENT DOCUMENTS
3,767,725 A    10/1973    Walker et al.

FOREIGN PATENT DOCUMENTS

| | | |
|---|---|---|
| DE | 285 770 | 7/1915 |
| EP | 0 718 544 | 6/1996 |
| EP | 0 856 698 | 8/1998 |
| EP | 0 982 282 | 3/2004 |
| WO | 2004/018400 | 3/2004 |

OTHER PUBLICATIONS

International Search Report for PCT/EP2007/002885, mailed Jul. 30, 2007.
Written Opinion of the International Searching Authority for PCT/EP2007/002885, mailed Jul. 30, 2007.
Thompson, A.F. et al., "The Preparation and Properties of Certain Acetylenic Tertiary Carbinols", J. Am. Chem. Soc., vol. 63, No. 1, pp. 186-188, (1941).
Huang, M. et al., "Reactions of Methylbutynol on Alkali-Exchanged Zeolites. A Lewis Acid-Base Selectivity Study", Catalysis Letters, vol. 18, pp. 373-389, (1993).

*Primary Examiner* — Tam M Nguyen
(74) *Attorney, Agent, or Firm* — Nixon & Vanderhye P.C.

(57) ABSTRACT

The present invention relates to a new method for a safe transport of ethyne in form of α-alkynols as precursors for ethyne. The new method comprises three steps. In a first step the synthesis of the α-alkynol(s) is performed by reacting ethyne with (a) carbonyl compound(s). The second step comprises the transport of the resulting α-alkynol(s) in a safe manner, whereas the safety requirements for this transport are not as high as for ethyne because α-alkynol(s) are normally classified for transportation as hazardous class 3. In the third step the α-alkynol(s) can be cleaved and the ethyne and the carbonyl compound(s) can be obtained in the cleavage reaction and can be separated to yield pure products for further applications.

17 Claims, 1 Drawing Sheet

TRANSPORT OF ETHYNE IN FORM OF α-ALKYNOLS AS ETHYNE PRECURSORS

Figure 1:
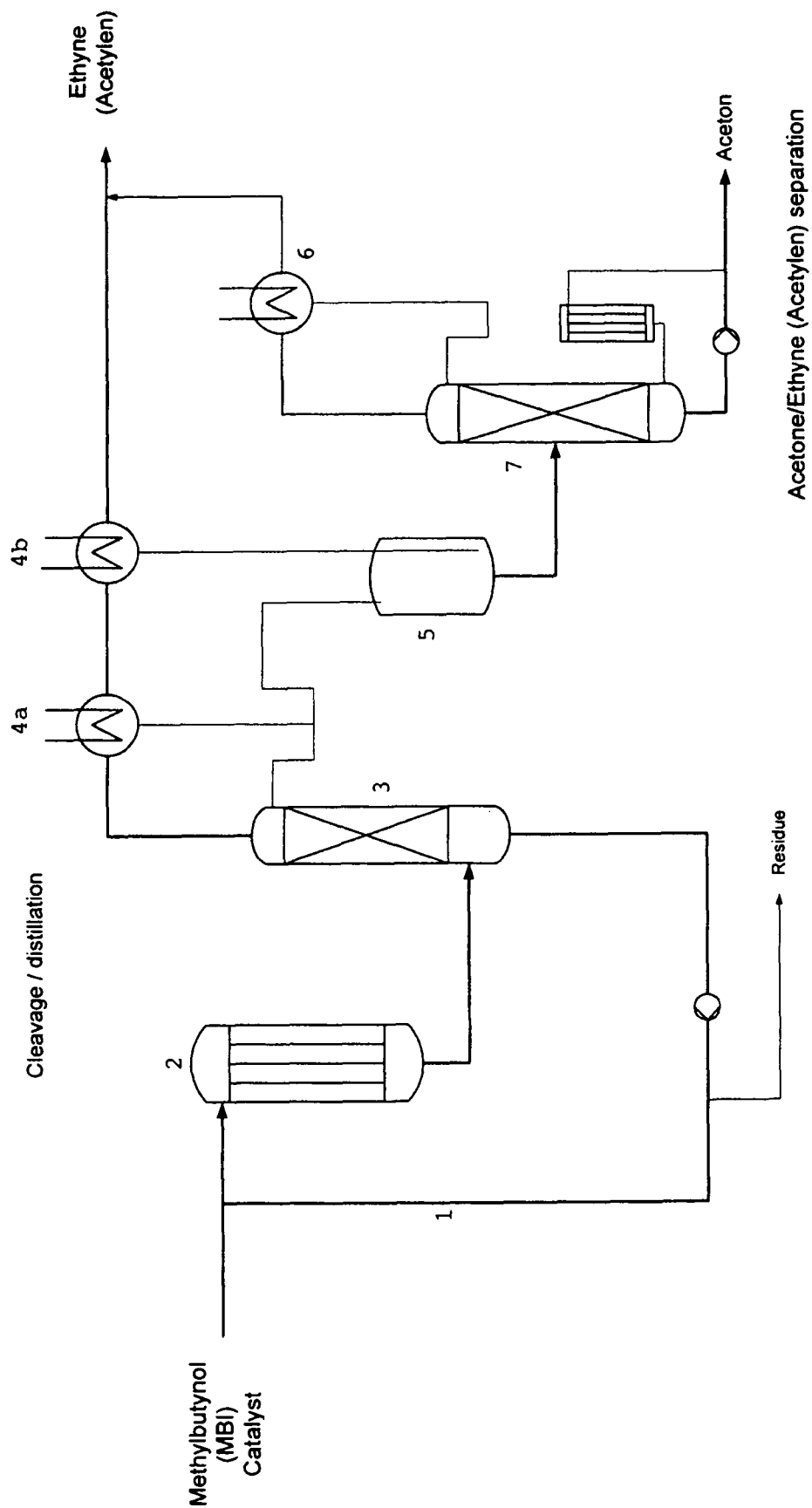

This application is the U.S. national phase of International Application No. PCT/EP2007/002885 filed 30 Mar. 2007 which designated the U.S. and claims priority to European Patent Application No. 06008477.9, filed 25 Apr. 2006, the entire contents of each of which are hereby incorporated by reference.

The present invention relates to a new method for a safe transport of ethyne, comprising the synthesis of (a) α-alkynol(s) by reacting ethyne with (a) carbonyl compound(s) and the transport of the resulting α-alkynol(s) in a safe manner, whereas the α-alkynol(s), can be seen as ethyne-precursors, and can be cleaved into ethyne and (a) carbonyl compound(s) after the transport and/or storage. The ethyne and the carbonyl compound(s) can be obtained in a cleavage reaction and can be separated to yield pure products for further applications.

Ethyne (acetylene) has various industrial applications for example the processing of metals, where the high flame temperature of ethyne is needed. Another example is the use of Ethyne in the production of plastic materials. However, the safe transport of ethyne is problematic because it is thermodynamically unstable and highly reactive. Because of its tendency to deflagrate or to detonate, ethyne cannot be compressed and stored in gas cylinders like other gases (Ullmann's Encyclopedia of Industrial Chemistry, $5^{th}$, completely revised edition, volume A1, page 135, 5.2). Therefore it has to be dissolved in solvents like for example acetone in order to be stored in gas cylinders. But also with this method many problems arise. For example if acetone is used as a solvent, the dissolving capacity is decreased by impurities. Furthermore any materials, used for ethyne cylinders have to be examined and approved prior to use, because interactions with the cylinder material and the ethyne must be avoided.

Because ethyne is considered as extremely flammable the classification of this gas is 2.1 (UN 1001), packaging group class 1. Contrary to this for example methylbutynol is classified for transportation under UN 1987 as class 3. To transport for example methylbutynol instead of ethyne results in less requirements for the containments because of the reduced safety regulations for class 3 compounds, which furthermore results in a more safe and cheaper transport. The same applies for other α-alkynols.

Therefore new methods for a safe transport of ethyne are very interesting for industrial applications. The present invention provides a method for a safe and economical transport of large ethyne quantities (preferably up to 100 t or even more) in form of α-alkynols. The synthesis of α-alkynols using ethyne as a starting material is known in the literature.

WO 03/029175 discloses a method for producing α-alkynols by reacting an aldehyde or a ketone with ethyne in the presence of ammonia and a strongly basic macroporous anion exchange resin (WO 03/029175 page 1, lines 7-10). The reaction products are for example used in the synthesis of terpenoids, e.g. vitamins and carotenoids. The strongly basic macroporous anion exchange resin is used as a catalyst in this ethynylation of carbonyl compounds. The method for the synthesis of α-alkynols according to WO 03/029175 is also suitable for the synthesis of α-alkynols according to the present invention.

Another method of this ethynylation process using alkali metal hydroxides as catalysts is disclosed in WO 2004/018400. This method also uses ethyne in the presence of ammonia and a carbonyl compound, wherein the molar ratio of the alkali metal hydroxide to the carbonyl compound is less than 1:200 (WO 2004/018400, page 1, lines 7 to 9). Again this method can be used for the present invention.

A further method which can be applied for the present invention, is disclosed in U.S. Pat. No. 2,163,720. Herein the process is conducted by reacting a saturated ketone with an alkali metal hydroxide such as potassium or sodium hydroxide, followed by a treatment of the resultant reaction mixture with acetylene (U.S. Pat. No. 2,163,720, column 1, lines 26 to 29). The resulting acetylenic alcohols are described as extremely valuable as starting materials in organic synthesis.

A process for preparing 1-ethynylcyclohexanol and homologues is described in GB 894,907. Using a condensed-phase technique provides a process to react alkyl-substituted cyclohexanones, whereas employing high temperatures provides good yields.

Another method for example to produce methylbutynol is disclosed in GB 1,342,166. This process also uses liquid ammonia and a gaseous mixture containing the alkyne and at least one alkene. This method can also be applied for the present invention.

The above-described α-alkynols are easier to handle and easier to store and much easier to transport without the above described safety risks of ethyne due to their lower reactivity. The drawbacks of the commonly used ethyne storage cylinders with their high safety requirements, which have to be approved by competent authorities are overcome by the possibility to use containments specified for hazardous class 3 and packaging group II compounds due to the use of α-alkynols as a non gaseous "transport-form" of ethyne.

After the transportation and prior to use, the α-alkynols which can be seen as stable precursors for ethyne, can be cleaved in a reverse process to yield ethyne and the carbonyl compounds. Analog to their synthesis a base catalysed process can be used for the cleavage reaction, which is known in the literature.

Huang et al. disclose a cleavage reaction of methylbutynol, using alkali-exchanged zeolites (Catalyses Letters, 1993, 18, 373-389). The alkali-exchanged zeolites have both Lewis acid and Lewis base centers, whereas the Lewis base centers catalyse the cleavage reaction of methylbutynol, which produces acetone and acetylene. This method can also be applied for the cleavage reaction according to the invention.

The present invention therefore provides a method for transport and storage of ethyne, using α-alkynols as a safe precursor for ethyne. The safety problems related with ethyne are overcome by the method of the present invention which comprises three steps. The first step comprises the synthesis of (a) α-alkynol(s) using ethyne and (a) carbonyl compound(s) and preferably a catalytic system. In a second step the α-alkynol(s), produced in the first step, is/are transported to its/their destination, where it/they will be used after applying the third step. Optionally the α-alkynol(s) can be stored, which is more safe than the storage of ethyne. The third step comprises the cleavage of the α-alkynol(s) into ethyne and (a) carbonyl compound(s), whereas pure ethyne and carbonyl compound(s) can be obtained. The compounds can then be used for further applications such as chemical synthesis.

The present invention relates to a method for a safe transport of ethyne, comprising the steps of:
i) synthesis of the α-alkynol(s) by reacting ethyne with (a) carbonyl compound(s),
ii) transport of the α-alkynol(s), and
iii) cleavage of the α-alkynol(s) into ethyne and carbonyl compound(s) after the transport.

In a preferred method the α-alkynol(s) are represented by the formula I:

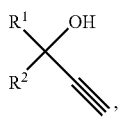

wherein $R^1$ and $R^2$ are independently selected from the group consisting of: hydrogen and hydrocarbon residues. Preferably the hydrocarbon residues contain 1-20 carbon atoms, more preferred are 1-15 carbon atoms, most preferred are 1-10 carbon atoms.

$R^1$ and $R^2$ in Formula I correspond to $R^1$ and $R^2$ in Formula II.

In one embodiment of the invention $R^1$ and $R^2$ are independently selected from the group consisting of:
hydrogen, linear order branched $C_{1-15}$-alkyl, $C_{1-15}$-aryl, $C_{1-15}$-aralkyl, $C_{1-15}$ alkylaryl, $C_{1-15}$-cycloalkyl, $C_{1-15}$-cycloalkenyl, $C_{1-15}$-alkenyl with 1 to 7 double bonds, preferably 1 to 4 double bonds and $C_{1-15}$-alkynyl groups with 1 to 3 triple bonds.

The carbonyl compounds according to the invention are represented by the formula II:

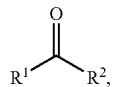

wherein $R^1$ and $R^2$ correspond to $R^1$ and $R^2$ of the α-alkynol(s), as specified above (corresponding to formula I).

More preferred is the method, wherein the α-alkynol(s) is/are selected from the group consisting of: methylbutynol, dehydrolinalool, dihydrodehydrolinalool, dihydroisophytol, ethynyl-β-ionol, ethynylphenylcarbinol (2-phenylbut-3-yne-2ol). Most preferred is that the α-alkynol is methylbutynol.

In an especially preferred embodiment, $R^1$ and $R^2$ of the carbonyl compound(s) and the α-alkynol(s) are selected from the group consisting of: hydrogen, methyl, ethyl, propyl, butyl, pentyl, and phenyl.

In another preferred embodiment of the invention the α-alkynol is methylbutynol, whereas $R^1$ and $R^2$ for the carbonyl compound and the α-alkynol are methyl radicals.

In a further preferred embodiment, the α-alkynol(s) is/are selected from the group consisting of: methylbutynol, dehydrolinalool, dihydrodehydrolinalool, dihydroisophytol, ethynyl-β-ionol, ethynylphenylcarbinol (2-phenylbut-3-yne-2ol).

In a preferred embodiment of the invention ethyne and a mixture of two carbonyl compounds is used for the synthesis of the α-alkynols, whereas a mixture of two α-alkynols is formed. Even more preferred is that only one carbonyl compound is used and only one α-alkynol is formed.

Preferred is the method, wherein the synthesis of the α-alkynol(s) is base catalysed.

In one embodiment of the invention the molar ratio carbonyl compound/catalyst is more than 250/1.

In a preferred embodiment the catalytic system is selected from the group consisting of: alkali metal hydroxides, anion exchange resins, basic polymers, solid bases.

Even more preferred is the method wherein the catalyst for the synthesis of the α-alkynol(s) is KOH.

Preferably the synthesis of the α-alkynol(s) is performed at temperatures between −20° C. and +50° C. It is more preferred that the synthesis of the α-alkynol(s) is performed at temperatures between 0° C. and +40° C. Most preferred is that the synthesis of the α-alkynol(s) is performed at temperatures between 15° C. and 30° C.

In another embodiment the synthesis of the α-alkynol(s) is performed at pressures between 5 to 50 bar. In a more preferred embodiment the synthesis of the α-alkynol(s) is performed at pressures between 10 to 30 bar.

Preferably the cleavage of the α-alkynol(s) is base catalysed.

In a preferred embodiment the cleavage of the α-alkynol(s) is performed at temperatures between 20° C. to 150° C. In a more preferred embodiment the cleavage of the α-alkynol(s) is performed at temperatures between 30° C. to 85° C.

Preferably the cleavage of the α-alkynol(s) is performed at a pressure between 50 mbar and normal atmospheric pressure (about 1013 mbar). More preferred the cleavage of the α-alkynol(s) is performed at normal atmospheric pressure (about 1013 mbar).

In one embodiment of the invention the ethyne and carbonyl compound(s) are continuously removed from the reaction mixture during the cleavage of the α-alkynol(s).

The method according to the present invention comprises synthesis, transport and cleavage of α-alkynols, whereas these three steps are described in more detail in the following.

The synthesis of α-alkynols for the use in the present invention can be performed by any process which uses ethyne and a carbonyl compound as starting materials. For example the above disclosed methods can be used to synthesize the α-alkynols. The ethyne can be directly introduced into the reaction mixture or can be dissolved in suitable solvents and can be added subsequently. Preferably ammonia is used as a solvent for the ethyne. The ammonia is used in the liquid state by appropriate choice of temperature and pressure, whereby at the same time an adequate acetylene pressure must also be provided and sustained in the reaction vessel. Furthermore mixtures of carbonyl compounds can be used.

The carbonyl compounds suitable for the synthesis of the α-alkynols are any aldehydes or ketones. Preferable organic carbonyl compounds can be defined by formula II:

II

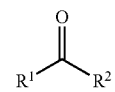

Wherein $R^1$ and $R^2$ can independently represent hydrogen or $C_{1-20}$-hydrocarbon residues. It is especially preferred that $R^1$ and $R^2$ are independently selected from hydrogen, linear or branched $C_{1-15}$-alkyl, $C_{1-15}$-aryl, $C_{1-15}$-aralkyl, $C_{1-15}$-alkylaryl, $C_{1-15}$-cycloalkyl, $C_{1-15}$-cycloalkenyl, $C_{1-15}$-alkenyl with 1 to 10 double bonds, and alkynyl groups.

$R^1$ and $R^2$ in Formula II correspond to $R^1$ and $R^2$ in Formula I.

It is even more preferred that $R^1$ and $R^2$ are selected from hydrogen, linear or branched $C_{1-10}$-alkyl, $C_{1-10}$-aryl, $C_{1-10}$-aralkyl, $C_{1-10}$-cycloalkyl, $C_{1-10}$-cycloalkenyl, $C_{1-10}$-alkenyl with 1 to 5 double bonds and alkynyl groups.

It is further preferred that $R^1$ and $R^2$ are selected from hydrogen, phenyl and linear or branched $C_{1-8}$-alkyl groups which are optionally substituted with phenyl groups.

The most preferable carbonyl compounds are acetone, methyl ethyl ketone, methyl propyl ketone, diethyl ketone, 6-methyl-5-hepten-2-one, formaldehyde, n-propanal, iso-butyraldehyde, n-butyraldehyde, acetaldehyde, benzaldehyde, hexahydropseudoionone, ethylheptenone, phytone, pseudoionone, pseudoirone, geranylacetone, farnesylacetone, 6,10-dimethyl-9-undecen-2-one, ketoisophorone, methylheptenone, methylheptanone, β-ionone, acetophenone. The resulting α-alkynols can be described by the formula, wherein $R^1$ and $R^2$ for the carbonyl compounds and for the α-alkynols are the same:

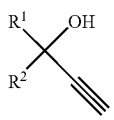  I

Wherein $R^1$ and $R^2$ can independently represent hydrogen or $C_{1-20}$ hydrocarbon residues. It is especially preferred that $R^1$ and $R^2$ are independently selected from hydrogen, linear or branched $C_{1-15}$-alkyl, $C_{1-15}$-aryl, $C_{1-15}$-aralkyl, $C_{1-15}$-alkylaryl, $C_{1-15}$-cycloalkyl, $C_{1-15}$-cycloalkenyl, $C_{1-15}$-alkenyl with 1 to 10 double bonds and $C_{1-15}$-alkynyl groups.

It is even more preferred that $R^1$ and $R^2$ are selected from: hydrogen, linear or branched $C_{1-10}$-alkyl, $C_{1-10}$-aryl, $C_{1-10}$-aralkyl, $C_{1-10}$-alkylaryl, $C_{1-10}$-cycloalkyl, $C_{1-10}$-cycloalkenyl, $C_{1-10}$-alkenyl with 1 to 5 double bonds, and $C_{1-10}$-alkynyl groups.

The most preferred α-alkynols are methylbutynol, dehydrolinalool, dihydrodehydrolinalool, dihydroisophytol, ethynyl-β-ionol, ethynylphenylcarbinol (2-phenylbut-3-yne-2ol), whereas methylbutynol is even more preferred.

Preferably in addition to ethyne and the carbonyl compound(s), the synthesis according to the invention uses a catalytic system. The reaction is preferably base catalysed whereas preferably alkali metal hydroxides, anion exchange resins, basic polymers, or solid bases can be used. Especially preferred as catalysts are alkali metal hydroxides, whereas potassium hydroxide is even more preferred.

As a preferred substrate catalyst ratio, a molar ratio carbonyl compound/catalyst of more than 250/1 can be selected.

Preferably the synthesis of the α-alkynols is performed at temperatures between −20° C. and +50° C., whereas a temperature range of 0° C. to +40° C. is even more preferred, and a temperature range between 15° C. and 30° C. is mostly preferred.

Preferably the synthesis of the α-alkynols is performed at pressures between 5-50 bar, even more preferably between 10 and 30 bar. The α-alkynols which are prepared in the first step, can be filled into suitable containments. The α-alkynols can be filled into the containments in pure form or dissolved in common organic solvents. Especially preferred is to store the α-alkynols in pure form.

The second step comprises the transport of the α-alkynol(s). The term "transport" refers to a transport of the α-alkynol(s) over a distance of at least 10 km, preferably at least 20 km and most preferably at least 50 km. The transport of the α-alkynols can be performed by all possible means of transportation in bulk or packed cargo, provided that transport- or packaging-units comply with respective international transport rules and regulations for transport of hazardous materials, which are: road (ADR), rail (RID), barge (ADNR), deep-sea (IMO IMDG), air (ICAO IATA). The preferred quantities of ethyne for transportation are quantities of more than 100 t, especially preferred more than 1000 t. The transport of the α-alkynols can also be performed by using pipelines. Furthermore the requirements for the storage of the α-alkynol(s) are lower compared to the requirements for ethyne. Therefore the α-alkynols are very suitable for storage before or after the transport.

The third step comprises the cleavage of the α-alkynol(s). The cleavage yields ethyne and (a) carbonyl compound(s), whereas preferably a mixture of two α-alkynols is used, even more preferred is the use of one α-alkynol, which leads to the formation of ethyne and one carbonyl compound.

Preferably in addition to the α-alkynols, a catalytic system is used. The cleavage reaction is preferably base catalyzed. Preferred catalytic systems are alkali metal hydroxides, anion exchange resins, basic polymers, hydrotalcid, potassium fluoride on aluminium oxide, and solid bases. The alkali metal hydroxides can be used in pure form or as a solution in water or alcohols, whereas the solution contains 1%-60%, preferred 10% to 50% of the alkali metal hydroxide.

The cleavage reaction is preferably carried out at a temperature between 20 and 150° C., even more preferred are temperatures between 50° C. and 95° C. and most preferred between 30° C. and 85° C.

Preferably the cleavage reaction is carried out at a pressure between 5 mbar and 1013 mbar (normal atmospheric pressure), even more preferred between 50 mbar and 1013 mbar. The cleavage reaction can be performed in a reaction device which can be stirred and heated under reflux. The charging of the reaction device can be performed by either adding the whole amount of α-alkynol(s) at once or divided in portions, or by a continuous feeding of the α-alkynols to the reaction device.

Preferably in addition the cleavage reaction is performed as a continuous process. FIG. 1 shows an example for a technical process. As the reaction is performed at elevated temperatures as defined above, it is possible to remove at least one of the products from the reaction mixture, because of its gaseous state. The catalyst remains in the reaction mixture. In an especially preferred embodiment both the ethyne and the carbonyl compound(s) can be distilled off from the reaction mixture at the reaction temperature, whereas the resulting compounds can be separated and purified by fractionated distillation. A further purification step can be applied to further purify the obtained fractions. Not reacted α-alkynol which might be contained in the gaseous product mixture can be returned to the reaction mixture.

The cleavage reaction yields ethyne and carbonyl compounds. Preferably these compounds are separated by distillation. The so formed ethyne can be dissolved in suitable solvents after cleavage of the α-alkynols or can be directly used for further applications. Preferred solvents for ethyne are DMF, NMP, acetone or THF.

EXAMPLE 1

Ethynylation of 6-methyl-5-hepten-2-one to produce 3,7-dimethyl-6-octen-1-yn-3-ol 796 mg of potassium hydroxide (KOH) in 45% (wt./vol.) aqueous solution and 194.5 g of 6-methyl-5-hepten-2-one (MH) were introduced into a reactor; the molar ratio KOH:MH was thus 1:250. After fourfold evacuation of the air from the reactor and subsequent flushing with nitrogen (inertisation of the reactor), 369 g of ammonia were introduced. Acetylene was then added to provide a pressure of 16.1 bar (1.61 MPa) at 30° C., corresponding to 21% (wt./vol.) of acetylene in the mixture of ammonia and acetylene. The contents of the reactor were agitated by gas stirring. Samples were taken at various time intervals for analysis of their content by gas chromatography (GC). After 5 hours the reaction was finally stopped since by then it had been established that a predominant amount of the desired product, 3,7-dimethyl-6-octen-1-yn-3-ol (dehydrolinalool; DLL) and only small amounts of diol by-product and unchanged MH were present. The results are presented in Table 1 below:

TABLE 1

Product composition vs. time [minutes (min.)/hour(s) (hr./hrs.)]

|  | 5 min. | 1 hr. | 2 hrs. | 5 hrs. |
|---|---|---|---|---|
| MH | 29.2 | 4.1 | 2.5 | 2.3 |
| DLL | 67.6 | 92.9 | 94.3 | 94.1 |
| Diol | 1.0 | 1.4 | 1.5 | 1.7 |

The synthesis of methylbutynol can be performed analog to the synthesis of 3,7-dimethyl-6-octen-1-yn-3-ol, wherein acetone is used instead of 6-methyl-5-hepten-2-one.

EXAMPLE 2

Procedure for Transport of Methylbutynol 50000 kg of pure methylbutynol are filled in a suitable containment according to UN 1987, class 3, TKGR II. The containment is suitable for transport by all possible means of transportation in bulk or packed cargo, provided that transport- or packaging-units comply with respective international transport rules and regulations- or transport of hazardous materials, which are: road (ADR), rail (RID), barch (ADNR), deep-sea (IMO IMDG), air (ICAO IATA).

Cleavage of Methylbutynol

EXAMPLE 3A

A 350 ml-four-necked flask (with heating-cooling jacket), equipped with a stirrer, thermometer (PT-100), inlet for substrate (dosimate, Metrohm 718 Stat Titrino), and vigreux columne (length 40 cm) was charged with 15 ml KOH (41.42% in $H_2O$, 0.154 mol) and heated up to 80° C. under stirring (750 rpm). Methylbutynol (MBI) was added during several hours (45 h) with a feed-rate of 0.8 ml/min (total 2160 ml, 22.11 mol). During the reaction acetone was distilled off and condensed using a cooling system (double surface condenser) at 0° C. The acetone fraction was stored at 0-5° C. (ice-bath). Yield acetone 1220 g 95%, not optimized. Yield ethyne 61 g (5%) in acetone, and 541 g (94%) collected in 13 l DMF (at 20° C.).

EXAMPLE 3B

A 250 ml-four-necked flask (with heating-cooling jacket), equipped with a stirrer, thermometer (PT-100), inlet for substrate (Gilson pump 305), and vigreux columne (length 40 cm) was charged with 30 ml KOH (41.42% in $H_2O$, 0.308 mol) and heated up to 84° C. under stirring (800 rpm). Methylbutynol (MBI) was added during several hours (12 h) with a feed-rate of 0.79 ml/min (total 567 ml, 5.8 mol). During the reaction acetone was distilled off and condensed using a cooling system (double surface condenser) at 0° C. The acetone fraction was stored at 0-5° C. (ice-bath). Yield acetone 316 g, 93.8%, not optimized. Yield ethyne 15.8 g (5%) in acetone, and 140.5 g (93%) collected in 3.5 l DMF (at 20° C.).

EXAMPLE 3C

A 100 ml-four-necked flask equipped with a thermometer, a reflux condenser, and a stirrer was charged with 17.22 g (205) mmol 2-methyl-3-butin-2-ol (MBI) stirred with 750 rpm, and heated up to reflux temperature. After 5 min an internal temperature of 90° C. was reached, and 2 g potassium fluoride on aluminium oxide (Fluka 60244, 21.5% KF) were added. The reaction was controlled by GC (samples were taken after 60 min, 155 min and 385 min). The ketones were separated by distillation. Yield acetone 11.47 g (96.5%), not optimized.

Cleavage of a Mixture of Two α-Alkynols

EXAMPLE 4A

A 100 ml-four-necked flask equipped with a thermometer, a reflux condenser, and a stirrer was charged with 8.61 g (102) mmol 2-methyl-3-butin-2-ol (MBI) and 15.58 g (102) mmol 3,7-dimethyl-6-octen-1-in-3-ol (DLL) stirred with 750 rpm and heated up to reflux temperature. After 5 min an internal temperature of 93° C. was reached, and 2 ml KOH (41.42% in $H_2O$, 20.53 mmol) were added. The reaction was controlled by GC (samples were taken after 60 min, 155 min and 385 min). The ketones were separated by distillation. Yield acetone 5.7 g, (95.8%), yield 6-methyl-5-hepten-2-on (MH) 12.3 g, (95.2%), not optimized.

EXAMPLE 4B

A 100 ml-four-necked flask equipped with a thermometer, a reflux condenser, and a stirrer was charged with 8.61 g (102) mmol 2-methyl-3-butin-2-ol (MBI) and 30.14 g (102 mmol) 3,7,11,15-tetramethyl-1-hexadecin-3-ol (DIP) stirred with 750 rpm and heated up to reflux temperature. After 5 min an internal temperature of 95° C. was reached, and 2 ml KOH (41.42% in $H_2O$, 20.53 mmol) were added. The reaction was controlled by GC (samples were taken after 60 min, 155 min and 385 min). The ketones were separated by distillation. Yield acetone 5.8 g, (97.5%), yield 6,10,14-trimethyl-2-pentadecanon ($C_{18}$—K) 26.1 g, (96.1%), not optimized.

EXAMPLE 5

Cleavage of Methylbutynol in a Continuous Process

The cleavage of methylbutynol can be performed in a continuous process for example like in FIG. 1. The reactor can be fed with methylbutynol and catalyst in a continuous manner. The cleavage of methylbutynol yields acetone and ethyne which are gases at suitable reaction temperatures. The gaseous products are directly removed from the reactor and separated by fractionated condensation, whereas ethyne stays gaseous and acetone and not reacted methylbutynol can be condensated. The methylbutynol can then be returned into the reaction mixture. The gaseous ethyne can be directly obtained as a pure product. The acetone still contains ethyne and the mixture is separated in a further purification step. After this second distillation step, pure acetone and ethyne can be obtained. The yield of ethyne is 95%.

Description of FIG. 1:

FIG. 1 shows the devices used for the technical process for the cleavage of α-alkynols. The technical elements in FIG. 1 are specified as: 1 (reactor loop), 2 (heat exchanger), 3 (column), 4a and 4b (heat exchanger), 5 (separator), 6 (heat exchanger), 7 (column).

The invention claimed is:

1. Method for a safe transport of ethyne, comprising the steps of:
   i) synthesis of α-alkynol(s) by reacting ethyne with (a) carbonyl compound(s),
   ii) transport of the α-alkynol(s), and iii) cleavage of the α-alkynol(s) into ethyne and carbonyl compound(s) after the transport.

2. Method according to claim 1, wherein the α-alkynol(s) are represented by the formula:

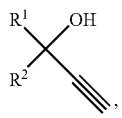

I wherein $R^1$ and $R^2$ are independently selected from the group consisting of hydrogen, linear oder branched $C_{1-15}$-alkyl, $C_{1-15}$-aryl, $C_{1-15}$-aralkyl, $C_{1-15}$-alkylaryl, $C_{1-15}$-cycloalkyl, $C_{1-15}$-cycloalkenyl, $C_{1-15}$-alkenyl with 1 to 7 double bonds, and $C_{1-15}$-alkynyl groups.

3. Method according to claim 1 wherein the carbonyl compound(s) are represented by the formula:

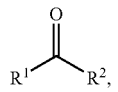

II wherein $R^1$ and $R^2$ are defined as $R^1$ and $R^2$ for the α-alkynol(s).

4. Method according to claim 1, wherein $R^1$ and $R^2$ are independently selected from the group consisting of:
hydrogen, linear oder branched $C_{1-10}$-alkyl, $C_{1-10}$-aryl, $C_{1-10}$-aralkyl, $C_{1-10}$-alkylaryl, $C_{1-10}$-cycloalkyl, $C_{1-10}$-cycloalkenyl, $C_{1-10}$-alkenyl with 1 to 5 double bonds, and $C_{1-10}$-alkynyl groups.

5. Method according to claim 1, wherein the synthesis of the α-alkynol(s) is base catalysed.

6. Method according to claim 5, wherein the molar ratio carbonyl compound/catalyst is more than 250/1.

7. Method according to claims 5, wherein the catalytic system is selected from the group consisting of: alkali metal hydroxides, anion exchange resins, basic polymers, solid bases.

8. Method according to claim 1, wherein the synthesis of the α-alkynol(s) is performed at temperatures between 0° C. and +40° C.

9. Method according to claim 1, wherein the synthesis of the α-alkynol(s) is performed at pressures between 10 to 30 bar.

10. Method according to claim 1, wherein the cleavage of the α-alkynol(s) is base catalysed.

11. Method according to claim 1, wherein the cleavage of the α-alkynol(s) is performed at temperatures between 20° C. to 150° C.

12. Method according to claim 1, wherein the cleavage of the α-alkynol(s) is performed at a pressure between 50 mbar and normal atmospheric pressure.

13. Method according to claim 1, wherein the ethyne and carbonyl compound(s) are removed from the reaction mixture during the cleavage of the α-alkynol(s).

14. Use of an α-alkynol as stable precursor for ethyne, wherein the α-alkynol is transported in a safe manner, and wherein the α-alkynol is cleaved into ethyne and a carbonyl compound after the transport, and wherein the α-alkynol is represented by the formula:

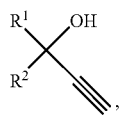

wherein $R^1$ and $R^2$ are independently selected from the group consisting of: hydrogen, phenyl, linear or branched $C_{1-8}$-alkyl radicals optionally substituted with phenyl radicals.

15. Use according to claim 14, wherein the cleavage of the α-alkynol is performed in a continuous process.

16. Use according to claim 15, wherein the continuous process comprises at least one purification step which is a fractionated distillation.

17. Use according to claims 14, wherein $R^1$ and $R^2$ are independently selected from the group consisting of: hydrogen, methyl, ethyl, propyl and phenyl.

* * * * *